United States Patent [19]

Horney

[11] Patent Number: 5,599,339
[45] Date of Patent: Feb. 4, 1997

[54] ABSORBENT ARTICLE

[75] Inventor: James C. Horney, Cincinnati, Ohio

[73] Assignee: The Procter & Gamble Company, Cincinnati, Ohio

[21] Appl. No.: 551,238

[22] Filed: Oct. 31, 1995

[51] Int. Cl.$^6$ .............................. A61F 13/15; A61F 13/20
[52] U.S. Cl. .................... 604/387; 604/385.1; 604/389
[58] Field of Search ................................. 604/358, 370, 604/372, 378, 385.1, 387, 389–390

[56] References Cited

U.S. PATENT DOCUMENTS

| | | | |
|---|---|---|---|
| 2,929,379 | 3/1960 | Poulsen | 604/370 |
| 3,367,334 | 2/1968 | Testa | 604/378 |
| 3,580,252 | 5/1971 | Delort. | |
| 4,094,316 | 6/1978 | Nathanson. | |
| 4,097,943 | 7/1978 | O'Connell. | |
| 4,161,176 | 7/1979 | Harris, II et al. | |
| 4,405,310 | 9/1983 | Karami. | |
| 4,425,130 | 1/1984 | Des Marais. | |
| 4,505,707 | 3/1985 | Feeney | 604/389 |
| 4,576,597 | 3/1986 | Hlaban | 604/389 |
| 4,605,404 | 8/1986 | Sneider. | |
| 4,657,538 | 4/1987 | Becker et al. | |
| 4,765,477 | 8/1988 | Froion et al. | |
| 4,806,411 | 2/1989 | Mattingly III et al. | |
| 4,938,756 | 7/1990 | Salek | 604/378 |
| 4,964,857 | 10/1990 | Osborn. | |
| 5,057,096 | 10/1991 | Faglione | 604/385.1 |
| 5,087,254 | 2/1992 | Davis et al. | |
| 5,429,631 | 7/1995 | Grenier | 604/385.1 |
| 5,458,591 | 10/1995 | Roessler et al. | |

FOREIGN PATENT DOCUMENTS

WO93/21878  11/1993  WIPO.
WO95/29655  11/1995  WIPO.

*Primary Examiner*—John G. Weiss
*Assistant Examiner*—P. Zuttarelli
*Attorney, Agent, or Firm*—Kevin C. Johnson; Steven W. Miller; Jacobus C. Rasser

[57] ABSTRACT

The present invention provides an absorbent article which includes a first absorbent article and a second absorbent article releasably secured to one another. The first and second absorbent articles are releasably secured to one another by at least one periphery securement member that is positioned along and extends outwardly from a portion of the periphery of the second absorbent article.

9 Claims, 5 Drawing Sheets

ABSORBENT ARTICLE

FIELD OF THE INVENTION

The present invention relates to absorbent articles such as incontinence pads, sanitary napkins, pantiliners, and the like, and more particularly to absorbent articles having a first absorbent article and a second absorbent article releasably secured to one another.

BACKGROUND OF THE INVENTION

Various absorbent articles such as sanitary napkins and light to medium incontinent devices exist which absorb body exudates such as menses, urine and fecal matter. Disposable products of this type generally comprise fluid permeable topsheet material, fluid absorbent core, and fluid impermeable backsheet material. Various shapes, sizes and thicknesses of such article have been explored in an attempt to make their use more comfortable and convenient. For example, U.S. Pat. No. 5,389,094, issued to Lavash et al., on Feb. 14, 1995; U.S. Pat. No. 5,383,869, issued to Osborn III on Jan. 24, 1995; U.S. Pat. No. 5,382,245, issued to Thompson et al., on Jan 17, 1995; and U.S. Pat. No. 5,346,486, issued Osborn III, et al., on Sep. 13, 1994, show numerous shapes, sizes, thicknesses and other alternative variations of absorbent articles.

There may be times when a user's needs may be variable or uncertain. At those times, a user may initially employ a first absorbent article, but may need to carry additional absorbent articles in reserve. Such is not always convenient, however. It would be desirable, then, for a user to be able to readily employ a second absorbent article after the first absorbent article has become soiled without having to retrieve the second absorbent article from reserve.

SUMMARY OF THE INVENTION

The present invention provides an absorbent article, comprising a first upper absorbent article having a length, a width, a periphery comprising a pair of end edges and a pair of longitudinal edges, a body facing surface and a garment facing surface. The first absorbent article includes a liquid pervious topsheet, a liquid impervious backsheet joined to the topsheet, and an absorbent core positioned between the topsheet and the backsheet.

The absorbent article further comprises a second lower absorbent article having a length which is less than the length of the first absorbent article, a width which is less than the width of the first absorbent article, a periphery comprising a pair of end edges and a pair of longitudinal edges, a body facing surface and a garment facing surface. The second absorbent article includes a liquid pervious topsheet, a liquid impervious backsheet joined to the top sheet, and an absorbent core positioned between the topsheet and the backsheet. The garment facing surface of the first absorbent article is positioned adjacent to the body facing surface of the second absorbent article. The longitudinal edges of the first and second absorbent articles are positioned substantially parallel to one another.

At least one periphery securement member releasably attaches to the first and second absorbent articles together. The securement member is positioned along and extends outwardly from a portion of the periphery of the second absorbent article.

In an alternative embodiment, at least one grasping means is attached to the first absorbent article, and at least one grasping means is attached to the second absorbent article. The grasping means for the first and second absorbent articles are located at a same end edge and are releasably attached to one-another by an attachment layer.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). As used herein, the term "sanitary napkin" or "napkin" refers to devices which absorb and contain body exudates, and more specifically, refers to an absorbent article which is worn by females adjacent to the pudendal region, generally external to the urogenital region, and which is intended to absorb and contain menstrual fluids and other vaginal discharges from the wearer's body (e.g., blood, menses, and urine). As used herein, the term "pudendal" refers to the externally visible female genitalia. It should be understood, however, that the present invention is also applicable to other feminine hygiene garments or catamenial pads such as pantiliners or other absorbent articles such as incontinence pads, and the like.

Figure 1:
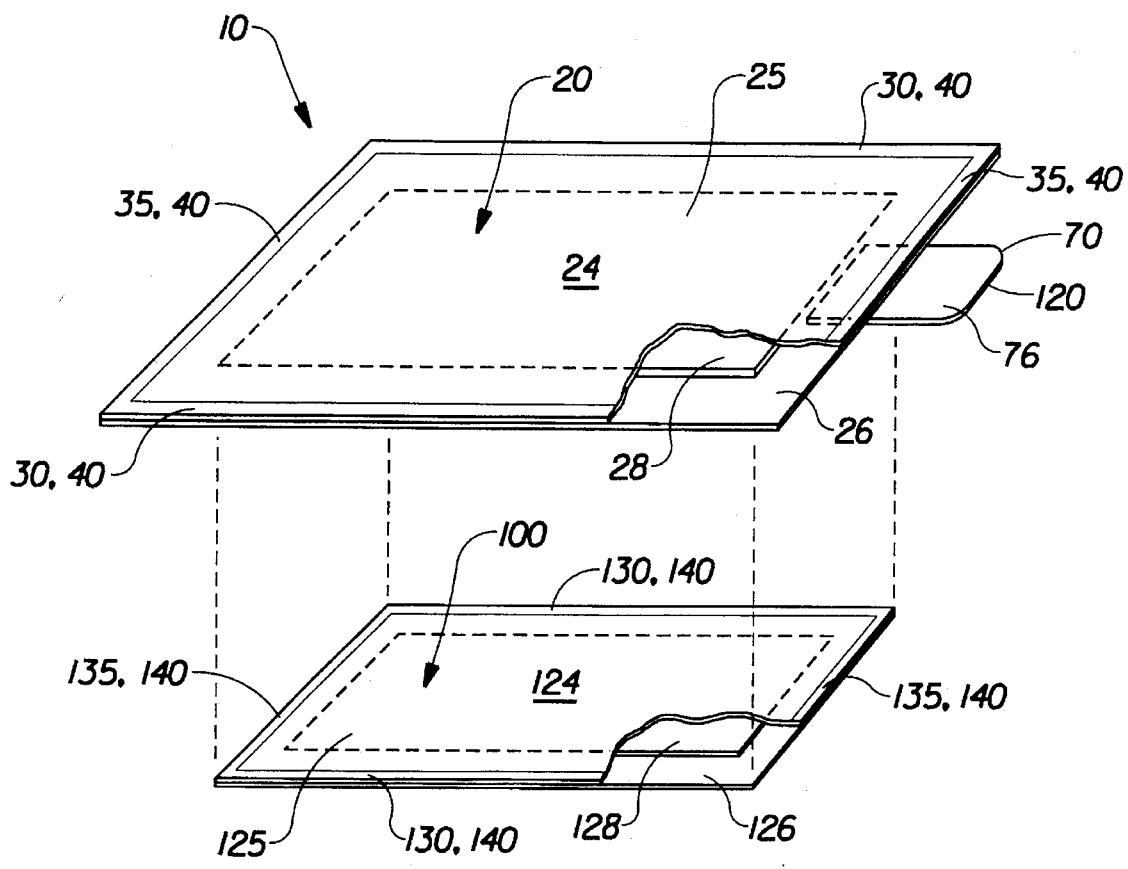
FIG. 1 is an exploded perspective view of the absorbent article of the present invention having portions cut away to reveal underlying structure.

FIG. 1 is an exploded perspective view of an absorbent article 10 of the present invention. The absorbent article 10 comprises a first, upper absorbent article 20 and a second, lower absorbent article 100. In the embodiment shown in FIG. 1, the first absorbent article 20 has length and width dimensions greater than those of the second absorbent article 100 so as to allow attachment via the securement member 200 (shown in FIG. 2), as will be discussed in greater detail hereinafter.

The first absorbent article 20 is shown in FIG. 1 with portions of the structure being cut-away to more clearly show the construction of the first absorbent article 20. The first absorbent article 20 preferably comprises a liquid pervious topsheet 24, a liquid impervious backsheet 26 joined with the topsheet 24, and an absorbent core 28 positioned between the topsheet 24 and the backsheet 26.

Figure 2:
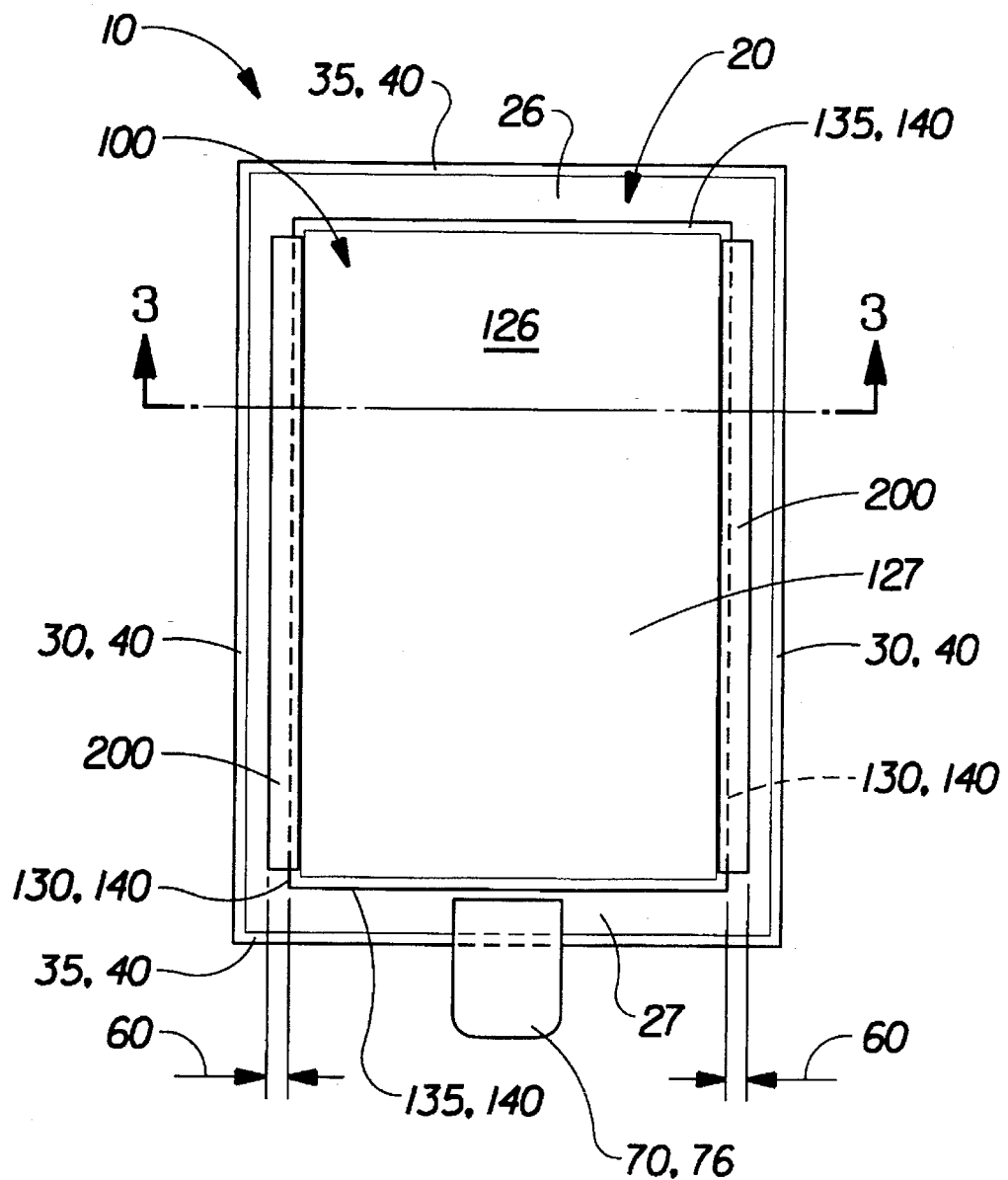
FIG. 2 is a plan view of the absorbent article of FIG. 1.

The first absorbent article 20 has two surfaces, a body facing surface or "body surface 25" and a garment facing surface 27 (shown in FIG. 2). The body facing surface 25 is intended to be worn adjacent to the body of the wearer while the garment facing surface 27 is on the opposite side and is intended to be placed adjacent to the second absorbent article 100. FIG. 1 also shows that the first absorbent article 20 has a periphery 40 which comprises longitudinal edges 30 and end edges 35.

While the topsheet, the backsheet, and the absorbent core may be assembled in a variety of well known absorbent article configurations (including so called "tube" products or side flap products), preferred absorbent article configurations are described generally in U.S. Pat. No. 4,950,264, "Thin, Flexible Sanitary Napkin" issued to Osborn on Aug. 21, 1990; U.S. Pat. No. 4,321,924, "Bordered Disposable Absorbent Article" issued to Ahr on Mar. 30, 1982; U.S. Pat. 4,589,876, "Shaped Sanitary Napkin With Flaps" issued to Van Tilburg on Aug. 18, 1987. Each of these patents are hereby incorporated herein by reference. FIG. 1 shows a preferred embodiment of the first absorbent article 20 in which the topsheet 24 and the backsheet 26 have length and width dimensions generally larger than those of the absorbent core 28. The topsheet 24 and the backsheet 26 extend beyond the edges of the absorbent core 28 to form portions of the periphery 40.

The absorbent core 28 may be any absorbent means which is capable of absorbing or retaining liquids (e.g., menses and/or urine). As shown in FIG. 1 the absorbent core 28 has a body surface, a garment surface, side edges, and end edges. The absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core 28 may also be varied (e.g., the absorbent core 28 may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 28 should, however, be compatible with the design loading and the intended use of the first absorbent article 20. Further, the size and absorbent capacity of the absorbent core 28 may be varied to accommodate different uses such as incontinence pads, pantiliners, regular sanitary napkins, or overnight sanitary napkins.

Most preferably, the absorbent core 28 comprises fluid distribution members comprising three basic components: chemically stiffened, twisted, and curled bulking fibers, high surface area fibers, and thermoplastic binder fibers. These fluid distribution members use a high surface fiber to provide the fluid distribution member with capillary pressure (or suction). These high surface are fibers are generally small and highly conformable. They provide the substrate with capillary pressure well in excess of the capillary pressure found in the bulk-providing chemically stiffened, twisted, and curled fibers alone.

A preferred fiber for this high surface application is the eucalyptus family of wood pulp fibers. Eucalyptus provides the capillary pressure usually associated with cellulose fines, but at a large enough length and denier so as to not fill in the voids provided by the chemically stiffened, twisted, and curled fibers and will not easily pass through the forming screen. Particularly suitable eucalyptus fibers include those of the eucalyptus grandis species. Exemplary fluid distribution members are described in U.S. patent application Ser. No. 08/382,817 filed Feb. 3, 1995, in the names of J. C. Horney and J. R. Noel, the disclosure of which is incorporated herein by reference.

Exemplary absorbent structures for use as the absorbent core 28 of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May. 30, 1989; and European Patent Application No. 0 198 683, The Procter & Gamble Company, published Oct. 22, 1986 in the name of Duenk, et al. Each of these patents are incorporated herein by reference.

The backsheet 26 and the topsheet 24 are positioned adjacent the garment surface and the body surface, respectively, of the absorbent core 28 and are preferably joined thereto and to each other by attachment means (not shown) such as those well known in the art. For example, the backsheet 26 and/or the topsheet 24 may be secured to the absorbent core 28 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague,. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the absorbent articles described herein such as pants, pajamas and undergarments. The backsheet 26 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Incorporated, of Terre Haute, Indiana under the designation XP-39385. The backsheet is preferably embossed and/or matte finished to provide a more clothlike appearance. Further, the backsheet 26 may permit vapors to escape from the absorbent core 28 (i.e., breathable) while still preventing exudates from passing through the backsheet 26.

The topsheet 24 is compliant, soft feeling, and non-irritating to the wearer's skin. Further, the topsheet 24 is liquid pervious permitting liquids (e.g., menses and/or urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929, 135, entitled "Absorptive Structures Having Tapered Capillaries", which issued to Thompson on Dec. 30, 1975; U.S. Pat. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference. The preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated herein by reference. Alternatively, the body surface of the topsheet can be made hydrophilic by treating it with a surfactant such as is described in the above referenced U.S. Pat. 4,950,254 issued to Osborn, incorporated herein by reference.

The second absorbent article 100 preferably comprises a liquid pervious topsheet 124, a liquid impervious backsheet 126 secured to the topsheet 124, and an absorbent core 128 positioned between the topsheet 124 and the backsheet 126.

The second absorbent article 100 has two surfaces, an absorbent article-contacting surface 125 which becomes a body facing or "body surface" at the removal of the first absorbent article 20 and a garment facing surface 127 (shown in FIG. 2). The second absorbent article 100 is shown in FIG. 1 with portions of the structure being cutaway to more clearly show the construction of the second absorbent article 100. The absorbent article-contacting surface is intended to be worn adjacent to the outer surface 27 of the first absorbent article 20, i.e., adjacent the outer surface of the backsheet 26. Upon removal of the first absorbent article 20 from a wearer's undergarment, the absorbent article-contacting surface of the second absorbent structure 100 will become the body facing surface 125 and will be worn adjacent to the wearer's body. FIG. 1 also shows that the second absorbent article 100 has a periphery 140 which comprises longitudinal edges 130 and end edges 135.

While the topsheet, the backsheet, and the absorbent core may be assembled in a variety of well known absorbent article configurations (including so called "tube" products or side flap products), preferred absorbent article configurations are described generally in U.S. Pat. No. 4,950,264, "Thin, Flexible Sanitary Napkin" issued to Osborn on Aug. 21, 1990; U.S. Pat. No. 4,321,924, "Bordered Disposable Absorbent Article" issued to Ahr on Mar. 30, 1982; U.S. Pat. No. 4,589,876, "Shaped Sanitary Napkin With Flaps" issued to Van Tilburg on Aug. 18, 1987. Each of these patents are hereby incorporated herein by reference. FIG. 1 shows a preferred embodiment of the second absorbent article 100 in which the topsheet 124 and the backsheet 126 have length and width dimensions generally larger than those of the absorbent core 128. The topsheet 124 and the backsheet 126 extend beyond the edges of the absorbent core 128 to form portions of the periphery 140.

The absorbent core 128 may be any absorbent means which is capable of absorbing or retaining liquids (e.g., menses and/or urine). As shown in FIG. 1 the absorbent core 28 has a body surface, a garment surface, side edges, and end edges. The absorbent core 128 may be manufactured in a wide variety of sizes and shapes (e.g., rectangular, oval, hourglass, dog bone, asymmetric, etc.) and from a wide variety of liquid-absorbent materials commonly used in various absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core 128 may also be varied (e.g., the absorbent core 128 may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 128 should, however, be compatible with the design loading and the intended use of the second absorbent article 100. Further, the size and absorbent capacity of the absorbent core 128 may be varied to accommodate different uses such as incontinence pads, pantiliners, regular sanitary napkins, or overnight sanitary napkins. The absorbent capacity of the absorbent core 128 may be the same as, greater than, or less than the absorbent capacity of the absorbent core 28 of the first absorbent article 20. Preferably, the absorbent capacity of the absorbent core 28 is less than the absorbent capacity of the absorbent core 28 as the first absorbent article 20 is intended to absorb more bodily fluid than the second absorbent article 100.

Most preferably, the absorbent core 128 comprises fluid distribution members comprising three basic components: chemically stiffened, twisted, and curled bulking fibers, high surface area fibers, and thermoplastic binder fibers. These fluid distribution members use a high surface fiber to provide the fluid distribution member with capillary pressure (or suction). These high surface are fibers are generally small and highly conformable. They provide the substrate with capillary pressure well in excess of the capillary pressure found in the bulk-providing chemically stiffened, twisted, and curled fibers alone.

A preferred fiber for this high surface application is the eucalyptus family of wood pulp fibers. Eucalyptus provides the capillary pressure usually associated with cellulose fines, but at a large enough length and denier so as to not fill in the voids provided by the chemically stiffened, twisted, and curled fibers and will not easily pass through the forming screen. Particularly suitable eucalyptus fibers include those of the eucalyptus grandis species. Exemplary fluid distribution members are described in U.S. patent application Ser. No. 08/382,817 filed Feb. 3, 1995 in the names of J. C. Horney and J. R. Noel, the disclosure of which is incorporated herein by reference.

Exemplary absorbent structures for use as the absorbent core 128 of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al. Each of these patents are incorporated herein by reference.

The backsheet 126 and the topsheet 124 are positioned adjacent the garment surface and the body surface, respectively, of the absorbent core 128 and are preferably joined thereto and to each other by attachment means (not shown) such as those well known in the art. For example, the backsheet 126 and/or the topsheet 124 may be secured to the absorbent core 128 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 126 is impervious to liquids (e.g., menses and/or urine) and is preferably manufactured from a thin plastic film, although other flexible liquid impervious materials may also be used. The backsheet 126 prevents the exudates absorbed and contained in the absorbent core 128 from wetting articles which contact the second absorbent article 100 such as pants, pajamas and undergarments. The backsheet 126 may thus comprise a woven or nonwoven material, polymeric films such as thermoplastic films of polyethylene or polypropylene, or composite materials such as a film-coated nonwoven material. Preferably, the backsheet 126 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Incorporated, of Terre Haute, Ind., under the designation XP-39385. The backsheet 126 is preferably embossed and/or matte finished to provide a more clothlike appearance. Further, the backsheet 126 may permit vapors to escape from the absorbent core 128 (i.e., breathable) while still preventing exudates from passing through the backsheet 126.

The topsheet 124 is compliant, soft feeling, and non-irritating to the wearer's skin. Further, the topsheet 124 is liquid pervious permitting liquids (e.g., menses and/or urine) to readily penetrate through its thickness. A suitable topsheet 124 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet 124 comprises an apertured formed film. Apertured formed films are preferred for the topsheet 124 because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in the preceding section First Absorbent Article Structure and each of these patents are incorporated herein by reference. The preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated herein by reference. Alternatively, the body surface of the topsheet can be made hydrophilic by treating it with a surfactant such as is described in the above referenced U.S. Pat. No. 4,950,254 issued to Osborn, incorporated herein by reference.

In a preferred embodiment of the present invention, an acquisition layer(s) may be positioned between the topsheets and the absorbent cores of the first absorbent article 20 and the second absorbent article 100, respectively. An acquisition layer may serve several functions including improving wicking of exudates over and into the absorbent core. There are several reasons why the improved wicking of exudates is important, including providing a more even distribution of the exudates throughout an absorbent core and allowing an absorbent article described herein to be made relatively thin. (The wicking referred to herein may encompass the transportation of liquids in one, two or all directions (i.e., in the x-y plane and/or in the z-direction). The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of absorbent articles disclosed herein having an acquisition layer and a topsheet are more fully described in U.S. Pat. No. 4,950,264 issued to Osborn and U.S. patent application Ser. No. 07/944,764, "Absorbent Article Having Fused Layers", filed Oct. 7, 1992, in the names of Cree, et al. Each of these references are incorporated herein by reference. In a preferred embodiment, the acquisition layer may be joined with the topsheet by any of the conventional means for joining webs together, most preferably by fusion bonds as is more fully described in the above-referenced Cree application.

Figure 3:
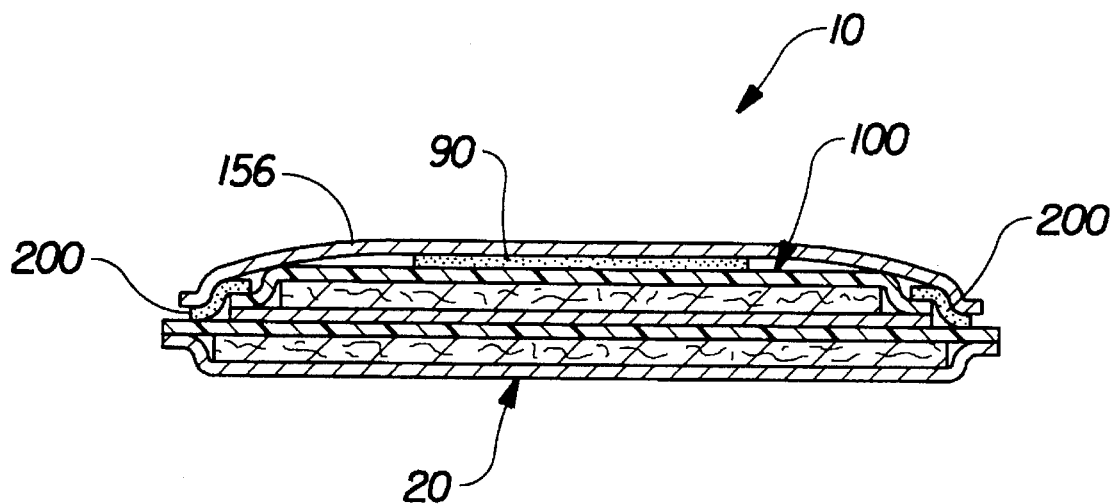
FIG. 3 is a cross-sectional view of the absorbent article taken along section line 3—3 of FIG. 2.

FIGS. 2 and 3 show absorbent articles 20 and 100 releasably secured to one-another such that after the first absorbent article 20 has been soiled, it may be separated from the second absorbent article 100, leaving the second absorbent article 100 in place in the user's panties. Securement members 200, are preferably positioned along and extend outwardly from the longitudinal edges 130 of the second absorbent article 100. The securement members 200 may comprise any suitable attachment means known in the art to be compatible with backsheet, topsheet and absorbent core materials. However, securement members 200 must extend outwardly from a portion of the periphery 140 of the second absorbent article 100 to join the first absorbent article 20 and the second absorbent article 100 together. As shown in FIGS. 2 and 3, the securement members 200 are joined to the backsheet 126 of the second absorbent article 100 extending outwardly beyond the longitudinal edges 130 where they are joined to the backsheet 26 of the first absorbent article 20. This configuration will provide sealing about the longitudinal edges 130 of the second absorbent article to keep it protected from soiling before its specified time of use.

In another embodiment, the securement members 200 may extend outwardly from the entire periphery 140, i.e., the longitudinal side edges 130 and end edges 135, of the second absorbent article 100. This configuration will provide sealing around and along the entire periphery 140 of the second absorbent article 100 to keep it protected from soiling before its specified time of use. In another embodiment, securement members 200 are positioned along and extend outwardly from the end edges 135 of the second absorbent article 100.

The securement means 200 may extend up to, but preferably not beyond the longitudinal edges 30 and/or end edges 35 of the first absorbent article 20. Suitable periphery securement means 200 may include any of the known bonding or attachment means for absorbent articles known in the art. The most preferred adhesive for use in the periphery securement means for this invention is a water-soluble adhesive such as Airflex 401 produced by Air Products & Chemicals, Incorporated, located in Allentown, Penn.

In use, the second absorbent article 100 can be held in place by any support means or attachment means 90 (shown in FIG. 3) well-known for such purposes. Preferably, the absorbent article 10, comprising the first absorbent article 20 and the second absorbent article 100 is placed in the user's undergarment or panty and secured thereto by a fastener located on the outer surface 127 of the backsheet 126 of the second absorbent article 100 such as an adhesive. The adhesive attachment means 90 or panty fastening adhesive provides a means for securing the second absorbent article 100 in the crotch portion of the panty. Thus, a portion or all of the outer surface 127 of the backsheet 126 comprises an adhesive attachment means 90. Any adhesive or glue used in the art for such purposes can be used for the adhesive attachment means 90 herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the second absorbent article 100 is placed in use, the pressure-sensitive adhesive attachment means 90 is typically covered with a removable release liner 156 in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. In a preferred embodiment, the second absorbent article 100 of the present invention is used by removing the release liners 156, and thereafter placing the second absorbent article 100 in a panty so that the adhesive attachment means 90 contacts the panty. As one function, the adhesive attachment means 90 maintains the second absorbent article 100 in its position within the panty during use.

Figure 4:
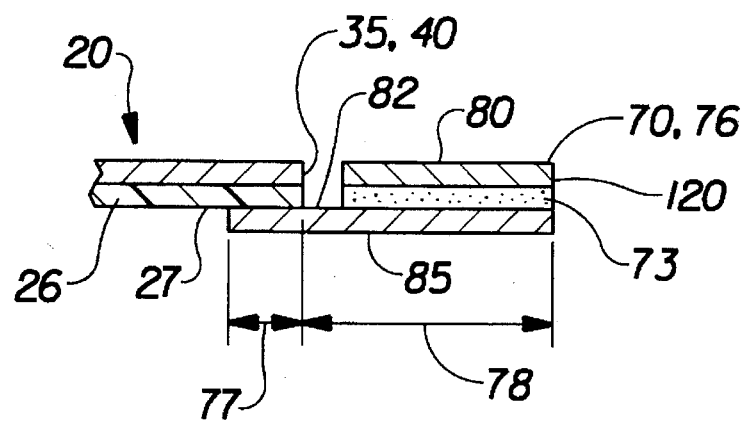
FIG. 4 is a fragmentary side view of the first absorbent article showing the grasping member.

In FIGS. 1, 2 and 4 there is shown a grasping member 70 which preferably comprises a tab 76. The tab 76 has a first surface 82 facing the wearer and a second surface 85 facing the garment. The tab 76 is joined to the backsheet 26 to create a fixed portion 77 (i.e., that portion of the tab 76 joined to the first absorbent article during manufacture). The tab 76 has another element which is the extended portion 78 which is that portion of the tab 76 which extends outwardly beyond the periphery of the first absorbent article and that is grasped by the user to separate the first absorbent article 20 from the second absorbent article. The distal end 120 of the tab 76 preferably has rounded corners to eliminate the possibility of harsh corner edges contacting the wearer's skin.

At least one tab 76 is joined to the first absorbent article 20, such that the extended portion 78 extends outwardly from an end edge of the absorbent article. Alternatively, the tab 76 may be joined to the absorbent article such that the extended portion 78 of the tab 76 extends outwardly from one of the longitudinal edges.

The fixed portion 77 is preferably joined to the outer surface of the backsheet of the first absorbent article 20. Alternatively, the fixed portion 77 may be joined to the first absorbent article by positioning the fixed portion 77 between the topsheet and the backsheet. While the fixed portion 77 may be joined directly to the body contacting surface of the topsheet, this is not preferred as the tab 76 may interfere with the fluid handling properties of the topsheet and may also be subjected to soiling. Also, but not preferably, the tab 76 may extend from the absorbent core or at least may have its fixed portion 77 located between the topsheet and backsheet, and thus extend outwardly therefrom; this configuration is also possible for any subsequent absorbent articles beyond the first and second absorbent articles as disclosed herein.

The tab 76 may also comprise a disposal means 73 joined to the first surface 82 of the extended portion 78 of tab 76. The disposal means 73 allows the first absorbent article 20 to be secured in a configuration that provides convenient disposal of the first absorbent article 20 and reduces leakage of liquid and/or solid exudates. Thus, the disposal means 73 may be any structure that allows the first absorbent article 20 to be folded or rolled up into a configuration for disposal and secured in that configuration. For example, the disposal means 73 may comprise a member of different elements positioned on the first surface 82 of the tab 76 such as an adhesive, or any other compatible element known to those of skill in the art. Compatible adhesives for the disposal means 73 can be, but are not limited to, Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Release member 80 protects the adhesive disposal means 73 from drying out prior to use. A suitable release member is described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis.

After the first absorbent article 20 has been soiled, the user removes the absorbent article 20 from his/her undergarment via the grasping member 70. At removal, the first absorbent article 20 is peeled or pulled away from the second absorbent article 100 preferably in a front (of user) to back (of user) motion. Upon removal of the first absorbent article 20, the adhesive disposal means 73 is exposed. The adhesive disposal means 73 most preferably attaches to the backsheet 26 of the first absorbent article 20 thus producing one that is folded at or near its lateral axis, or it is tri-folded along two axis parallel to the lateral axis, or is rolled in a circular configuration. The folded and sealed absorbent article 20 has its backsheet 26 as the exterior surface, and its topsheet 24 as the interior and soiled surface. The absorbent article 20 is now ready for disposal and remains sealed, and thereby at least partially reduces liquid, solid and vapor leakage.

A grasping member 70 will most preferably comprise polyethylene, but can alternatively comprise paper and/or cloth. Furthermore, the grasping member 70 can be an extension of the backsheet 26, topsheet 24 or core 28. In alternative embodiments the grasping member 70 can be positioned on the longitudinal edges 30 and 130 of the first and second absorbent articles 20 and 100, respectively. For an absorbent article which includes flaps, grasping members 70 can be placed on the flaps 54 and/or along the longitudinal edges 30. Disposal means 73 can be included on each of the grasping members 70.

In an alternative embodiment, the disposal means 73 is a mechanical loop or hook type as disclosed in U.S. Pat. No. 5,058,247 entitled "Mechanical Fastening Prong" issued to Thomas Oct. 22, 1991; U.S. Pat. No. 4,869,724 entitled "Mechanical Fastening Systems With Adhesive Tape Disposal Means For Disposal of Absorbent Articles" issued to Scripps on Sep. No. 26, 1989; and U.S. Pat. No. 4,846,815 entitled "Disposable Diaper Having an Improved Fastening Device" issued to Scripps on Jul. 11, 1989 and are incorporated herein by reference. For a hook disposal means 73, loops will on the backsheet and optimally placed to receive the hooks. For a loop disposal means 73, hooks will be on the backsheet and optimally placed to receive the loops.

Figure 5:
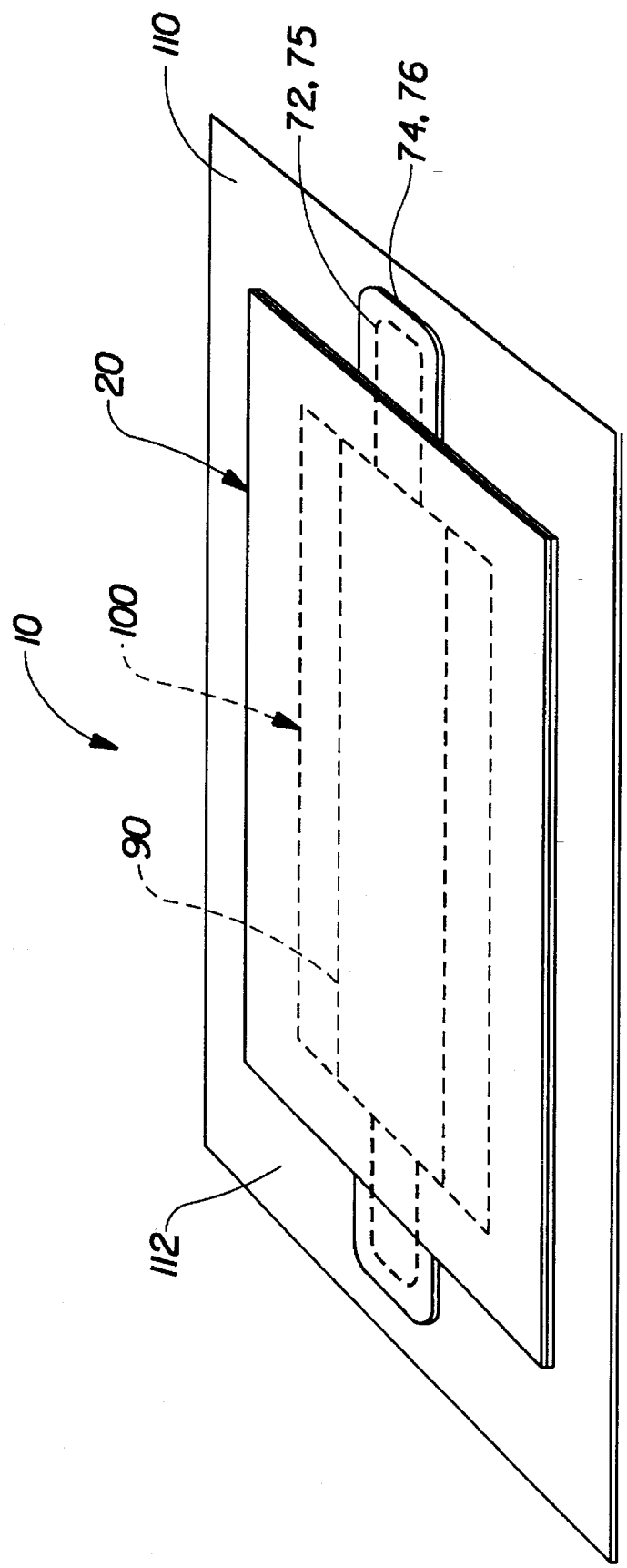
FIG. 5 is a perspective view of another embodiment of an absorbent article of the present invention.

FIG. 5 discloses another embodiment of an absorbent article 10 comprising first absorbent article 20 and second absorbent article 100. Absorbent articles 20 and 100 each have grasping members 72 and 74 which preferably are tabs 75 and 76, respectively. Tab 76 on second absorbent article 100 also secures the first and second absorbent articles together. The tab 76 on the second absorbent article 100 extends outwardly from the end edges of the second absorbent article 100 to join the first and second absorbent articles 20 and 100 together.

Figure 6B:
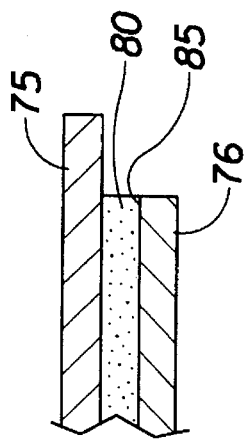
FIG. 6B is a fragmentary side view of the first tab and the second tab having an attachment layer therebetween.

FIG. 6B illustrates a preferred tab arrangement wherein tab 76 is releasably adhered to tab 75. Tab 75 comprises an attachment layer 80 (preferably an adhesive) positioned on its surface facing tab 76 and which becomes releasably attached to attachment surface 85. Preferably, attachment layer 80 is a panty fastening adhesive of the type disclosed herein. In a preferred embodiment, attachment surface 85 comprises a release surface at least partially comprising material similar to or the same as that of a release liner. Suitable release liners are described in U.S. Pat. No. 4,917, 697 and U.S. Pat. No. 4,556,146. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis.

Figure 6A:
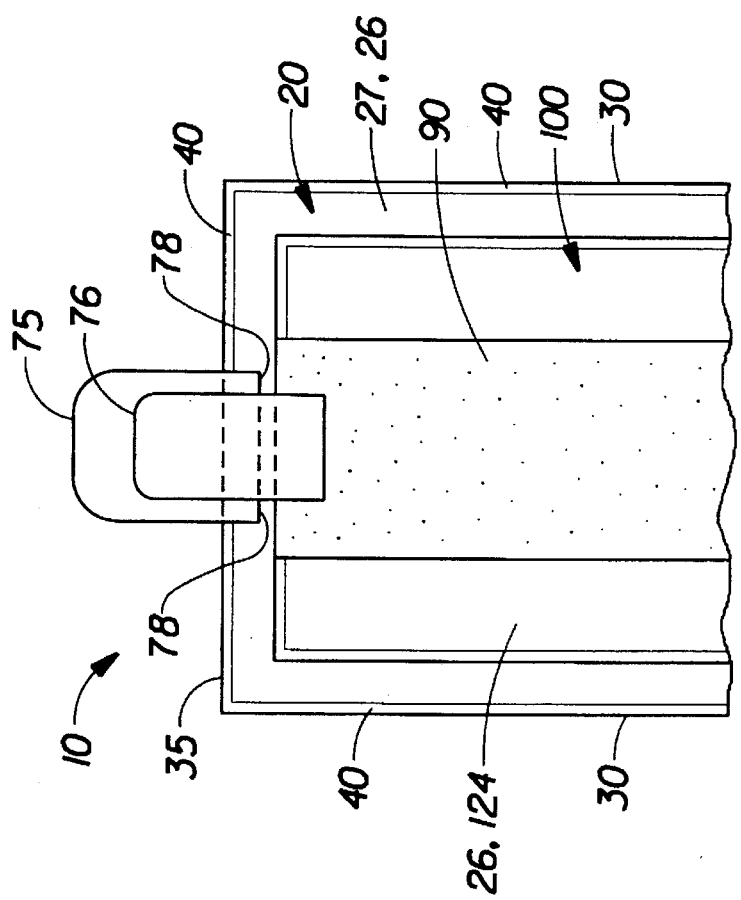
FIG. 6A is a fragmentary plan view of the absorbent article of FIG. 5 having the release paper removed or viewed from the garment facing surface of the absorbent article.

Referring to FIG. 5 and 6A, second absorbent article 100 comprises a panty fastening adhesive or attachment means 90 which can be any of the known adhesives for attaching an absorbent article to a garment. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. The attachment means 90 is most preferably affixed to the garment surface of the backsheet of the second absorbent article 100. For placement of the absorbent article 10 into an undergarment, a user can detach the absorbent article 10 from the release paper 110 by grasping the attached tabs 75 and 76, and then gently pull the absorbent article 10 up and away from the release paper 110, Note, it may be necessary for a user to hold the release paper 110 fixed while disengaging the absorbent article 10 from the release paper 110. In an alternative embodiment, the second tab 75 can have an adhesive (not shown) the same as or having similar properties to the adhesive 80 located on the garment surface 127 of the second absorbent article 100. This adhesive 81 would additionally serve to releasably attach absorbent article 10 to a user's undergarment.

FIG. 6A discloses a fragmented plan view of the embodiment of the present invention wherein the first absorbent article 20 and the second absorbent article 100 are releasably attached by first and second tabs 75 and 76, respectively. Tab 75 extends outwardly from the first absorbent article 10 at an end edge 35. Preferably, tab 75 has its attached end 78 attached to the backsheet 26 of the first absorbent article 20. From this point of attachment, the tab 75 extends outwardly from the end edge 35. As mentioned, the most preferably arrangement for tab releasable attachment is by that embodiment shown in FIG. 5B; i.e., the first tab 75 comprises an adhesive 80 and the second tab 76 comprises an attachment surface 85 which receives the adhesive 80. Alternative tab embodiments include mechanical fastener types such as hook and loop fasteners. For example, the first tab 75 can at least partially comprise hooks, while the second tab 76 can at least partially comprise corresponding loops. Note, it would be obvious to alternative and/or combine hooks, loops and adhesives amongst the tabs. Any mechanical fasteners known in the art are suitable for the invention disclosed herein, and examples include those of mechanical closure systems disclosed in U.S. Pat. No. 4,869,724 issued to Scripps on Sep. 9, 1989; U.S. Pat. No. 4,848,815 issued to Scripps on Jul. 11, 1989 and the two-point securement system described in U.S. Pat. No. 5,242,436 issued to Weil, Buell, Clear, and Falcone on Sep. 7, 1993 each of which are incorporated herein by reference.

In an alternative embodiment of the present invention, at least one of the absorbent articles described herein, can have two flaps, each of which are adjacent to and extend laterally from the longitudinal edges of the absorbent core. The flaps are configured to drape over the edges of the wearer's panties in the crotch region so that the flaps are disposed between the edges of the wearer's panties and the thighs. The flaps serve at least two purposes. First, the flaps help serve to prevent soiling of the wearer's body and panties by menstrual fluid, preferably by forming a double wall barrier along the edges of the panty. Second, the flaps are preferably provided with attachment means, and preferably adhesive, on their garment surface so that the flaps can fold back under the panty and attach to the garment facing side of the panty or one flap to another. In this way, the flaps serve to keep the second absorbent article properly positioned in the panty. The flaps can be constructed of various materials including materials similar to the topsheet, backsheet, tissue, or combination of these materials. Further, the flaps may be a separate element attached to the main body of the first absorbent article and/or second absorbent article or can comprise extensions of their respective topsheets and backsheets (i.e., a unitary construction). A number of sanitary napkins having flaps suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; U.S. Pat. No. 4,589,876 entitled "Sanitary Napkin", which issued to Van Tilburg on May. 20, 1986; and U.S. Pat. No. 4,608,047, entitled "Sanitary Napkin Attachment Means", which issued to Mattingly on Aug. 26, 1986. Each of these patents are incorporated herein by reference.

The number of absorbent articles which can be used and releasably secured together ranges from 2 to 15, most preferably, the range is from 2 to 3. All subsequent absorbent articles will be releasably secured together as described above with respect to the releasable securement of the first and second absorbent articles 20 and 100.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article, comprising:

a first upper absorbent article having a length, a width, a periphery comprising a pair of end edges and a pair of longitudinal edges, a body facing surface and a garment facing surface, said first absorbent article comprising a liquid pervious topsheet, a liquid impervious backsheet joined to said topsheet, and an absorbent core positioned between said topsheet and said backsheet;

a second lower absorbent article having a length which is less than the length of said first absorbent article, a width which is less than the width of said first absorbent article, a periphery comprising a pair of end edges and a pair of longitudinal edges, a body facing surface and a garment facing surface, said second absorbent article comprising a liquid pervious topsheet, a liquid impervious backsheet joined to said topsheet, and an absorbent core positioned between said topsheet and said backsheet, said garment facing surface of said first absorbent article being positioned adjacent to said body facing surface of said second absorbent article, said longitudinal edges of said first and second absorbent articles being positioned substantially parallel to one another; and at least two periphery securement members releasably attaching said first and second absorbent articles together, said securement members positioned on said backsheet of said second absorbent article, said securement members extending outwardly from said longitudinal edges of said second absorbent article onto said backsheet of said first absorbent article, said securement members providing a protective seal along said longitudinal edges against contamination of said second absorbent article prior to its use.

2. The absorbent article of claim 1 wherein said securement members are positioned on said backsheet of said second absorbent article, said securement members extending outwardly from said end edges of said second absorbent article onto said backsheet of said first absorbent article, said securement members providing a protective seal along said end edges against contamination of said second absorbent article prior to its use.

3. The absorbent article of claim 1 wherein said securement member comprises an adhesive.

4. The absorbent article of claim 1 wherein said backsheet of said second absorbent article comprises a panty fastening adhesive.

5. The absorbent article of claim 4 wherein said absorbent article comprises a release liner joined to said panty fastening adhesive.

6. The absorbent article of claim 1 further comprising at least one grasping means disposed on said first absorbent article.

7. The absorbent article of claim 1 further comprising at least one grasping means disposed on said second absorbent article.

8. The absorbent article of claim 7 wherein said grasping means comprises a tab.

9. The absorbent article of claim 1 wherein said absorbent article is releasably attached to a release paper prior to its placement in a user's undergarment.

* * * * *